(12) United States Patent
Mullen et al.

(10) Patent No.: US 9,384,438 B2
(45) Date of Patent: Jul. 5, 2016

(54) CARDS WITH SERIAL MAGNETIC EMULATORS

(75) Inventors: Jeffrey D. Mullen, Pittsburgh, PA (US); David Lambeth, Pittsburgh, PA (US); Ryan Kellogg, Pittsburgh, PA (US)

(73) Assignee: DYNAMICS, INC., Pittsburgh, PA (US)

( * ) Notice: Subject to any disclaimer, the term of this patent is extended or adjusted under 35 U.S.C. 154(b) by 0 days.

(21) Appl. No.: 13/186,469

(22) Filed: Jul. 20, 2011

(65) Prior Publication Data

US 2011/0272473 A1    Nov. 10, 2011

Related U.S. Application Data

(63) Continuation of application No. 12/339,042, filed on Dec. 19, 2008.

(60) Provisional application No. 61/016,491, filed on Dec. 24, 2007, provisional application No. 61/026,846,
(Continued)

(51) Int. Cl.
*G06K 19/06* (2006.01)
*G06K 19/077* (2006.01)
(Continued)

(52) U.S. Cl.
CPC .... *G06K 19/07709* (2013.01); *G06K 19/06206* (2013.01); *G06K 19/07* (2013.01); *G06K 19/07703* (2013.01); *G06K 19/07705* (2013.01); *G06K 19/07707* (2013.01); *G06K 19/07749* (2013.01); *G06Q 20/18* (2013.01); *G06Q 20/20* (2013.01); *G06Q 20/34* (2013.01); *G06Q 20/341* (2013.01); *G06Q 20/3415* (2013.01); *G06Q 20/352* (2013.01); *G06Q 20/385* (2013.01); *G06Q 30/0222* (2013.01);
(Continued)

(58) Field of Classification Search
USPC .............. 235/487, 492; 340/572.1, 572.4
See application file for complete search history.

(56) References Cited

U.S. PATENT DOCUMENTS

| | | | |
|---|---|---|---|
| 3,955,180 A | 5/1976 | Hirtle | |
| 4,328,415 A | 5/1982 | Eaton | |

(Continued)

FOREIGN PATENT DOCUMENTS

| | | |
|---|---|---|
| EP | 0203683 | 12/1986 |
| GB | 2420098 | 5/2006 |

(Continued)

OTHER PUBLICATIONS

U.S. Appl. No. 60/549,300, Poidomani et al.
(Continued)

*Primary Examiner* — Daniel Hess
*Assistant Examiner* — Tabitha Chedekel

(57) ABSTRACT

A card is provided, such as a credit card or security card, that may transmit information to a magnetic stripe reader via a magnetic emulator. The emulator may transmit the information serially in order to reduce the amount of circuitry needed to emulate a particular block of information. Additionally, for example, a serial encoder may send any amount of information through a single emulation segment. Such a magnetic emulator may be provided on a credit card. A dynamic credit card number may be provided by, for example, coding a number with a different coding scheme for different periods of time. The magnetic emulator may be utilized to transmit a particular coded number for a particular period of time. In this manner, a dynamic credit card number may be provided such that to help secure, and progress, a payment transaction.

20 Claims, 8 Drawing Sheets

Related U.S. Application Data filed on Feb. 7, 2008, provisional application No. 61/027,807, filed on Feb. 11, 2008, provisional application No. 61/081,003, filed on Jul. 15, 2008, provisional application No. 61/086,239, filed on Aug. 5, 2008, provisional application No. 61/090,423, filed on Aug. 20, 2008, provisional application No. 61/097,401, filed on Sep. 16, 2008, provisional application No. 61/112,766, filed on Nov. 9, 2008, provisional application No. 61/117,186, filed on Nov. 23, 2008, provisional application No. 61/119,366, filed on Dec. 2, 2008, provisional application No. 61/120,813, filed on Dec. 8, 2008.

(51) Int. Cl.

| | | |
|---|---|---|
| G06K 19/07 | (2006.01) | |
| G06Q 20/18 | (2012.01) | |
| G06Q 20/20 | (2012.01) | |
| G06Q 20/34 | (2012.01) | |
| G06Q 20/38 | (2012.01) | |
| G06Q 30/02 | (2012.01) | |
| G06Q 30/06 | (2012.01) | |
| G07F 7/08 | (2006.01) | |
| G07F 7/10 | (2006.01) | |

(52) U.S. Cl.
CPC ....... *G06Q 30/0241* (2013.01); *G06Q 30/0277* (2013.01); *G06Q 30/0641* (2013.01); *G07F 7/0806* (2013.01); *G07F 7/1008* (2013.01)

(56) References Cited

U.S. PATENT DOCUMENTS

| | | | |
|---|---|---|---|
| 4,353,064 A | 10/1982 | Stamm | |
| 4,394,654 A | 7/1983 | Hofmann-Cerfontaine | |
| 4,587,410 A | 5/1986 | Milnes | |
| 4,614,861 A | 9/1986 | Pavlov et al. | |
| 4,667,087 A | 5/1987 | Quintana | |
| 4,701,601 A | 10/1987 | Francini et al. | |
| 4,720,860 A | 1/1988 | Weiss | |
| 4,786,791 A | 11/1988 | Hodama | |
| 4,789,776 A | 12/1988 | Inoue | |
| 4,791,283 A | 12/1988 | Burkhardt | |
| 4,797,542 A | 1/1989 | Hara | |
| 4,902,146 A | 2/1990 | Ishikawa | |
| 4,931,991 A | 6/1990 | Cvijanovich | |
| 5,038,251 A | 8/1991 | Sugiyama et al. | |
| 5,166,774 A | 11/1992 | Banerji et al. | |
| 5,168,520 A | 12/1992 | Weiss | |
| 5,237,614 A | 8/1993 | Weiss | |
| 5,254,843 A | 10/1993 | Hynes et al. | |
| 5,276,311 A | 1/1994 | Hennige | |
| 5,347,580 A | 9/1994 | Molva et al. | |
| 5,361,062 A | 11/1994 | Weiss et al. | |
| 5,412,199 A | 5/1995 | Finkelstein et al. | |
| 5,434,398 A | 7/1995 | Goldberg | |
| 5,434,405 A | 7/1995 | Finkelstein et al. | |
| 5,477,038 A | 12/1995 | Levine et al. | |
| 5,478,994 A | 12/1995 | Rahman | |
| 5,479,512 A | 12/1995 | Weiss | |
| 5,484,997 A | 1/1996 | Haynes | |
| 5,485,519 A | 1/1996 | Weiss | |
| 5,521,831 A | 5/1996 | May | |
| 5,585,787 A | 12/1996 | Wallerstein | |
| 5,591,949 A | 1/1997 | Bernstein | |
| 5,608,203 A | 3/1997 | Finkelstein et al. | |
| 5,623,552 A | 4/1997 | Lane | |
| 5,657,388 A | 8/1997 | Weiss | |
| 5,748,737 A | 5/1998 | Daggar | |
| 5,834,747 A | 11/1998 | Cooper | |
| 5,834,756 A | 11/1998 | Gutman et al. | |
| 5,838,549 A | 11/1998 | Nagata et al. | |
| 5,856,661 A | 1/1999 | Finkelstein et al. | |
| 5,864,623 A | 1/1999 | Messina et al. | |
| 5,886,874 A | 3/1999 | Onoda et al. | |
| 5,907,142 A | 5/1999 | Kelsey | |
| 5,913,203 A | 6/1999 | Wong et al. | |
| 5,937,394 A | 8/1999 | Wong et al. | |
| 5,955,021 A | 9/1999 | Tiffany, III | |
| 5,955,961 A | 9/1999 | Wallerstein | |
| 5,956,699 A | 9/1999 | Wong et al. | |
| 6,012,636 A | 1/2000 | Smith | |
| 6,025,054 A | 2/2000 | Tiffany, III | |
| 6,045,043 A | 4/2000 | Bashan et al. | |
| 6,076,163 A | 6/2000 | Hoffstein et al. | |
| 6,085,320 A | 7/2000 | Kaliski | |
| 6,095,416 A | 8/2000 | Grant et al. | |
| 6,129,277 A | 10/2000 | Grant et al. | |
| 6,130,621 A | 10/2000 | Weiss | |
| 6,145,079 A | 11/2000 | Mitty et al. | |
| 6,157,920 A | 12/2000 | Jakobsson et al. | |
| 6,161,181 A | 12/2000 | Haynes, III et al. | |
| 6,176,430 B1 | 1/2001 | Finkelstein et al. | |
| 6,182,894 B1 | 2/2001 | Hackett et al. | |
| 6,189,098 B1 | 2/2001 | Kaliski | |
| 6,193,163 B1 | 2/2001 | Fehrman et al. | |
| 6,199,052 B1 | 3/2001 | Mitty et al. | |
| 6,206,293 B1 | 3/2001 | Gutman et al. | |
| 6,240,184 B1 | 5/2001 | Huynh et al. | |
| 6,241,153 B1 | 6/2001 | Tiffany, III | |
| 6,256,873 B1 | 7/2001 | Tiffany, III | |
| 6,269,163 B1 | 7/2001 | Rivest et al. | |
| 6,286,022 B1 | 9/2001 | Kaliski et al. | |
| 6,308,890 B1 | 10/2001 | Cooper | |
| 6,313,724 B1 | 11/2001 | Osterweil | |
| 6,389,442 B1 | 5/2002 | Yin et al. | |
| 6,393,447 B1 | 5/2002 | Jakobsson et al. | |
| 6,402,029 B1 | 6/2002 | Gangi | |
| 6,411,715 B1 | 6/2002 | Liskov et al. | |
| 6,446,052 B1 | 9/2002 | Juels | |
| 6,460,141 B1 | 10/2002 | Olden | |
| 6,554,193 B1 | 4/2003 | Fehrman et al. | |
| 6,592,044 B1 | 7/2003 | Wong et al. | |
| 6,607,127 B2 | 8/2003 | Wong | |
| 6,609,654 B1 | 8/2003 | Anderson et al. | |
| 6,631,849 B2 | 10/2003 | Blossom | |
| 6,655,585 B2 | 12/2003 | Shinn | |
| 6,681,988 B2 | 1/2004 | Stack et al. | |
| 6,705,520 B1 | 3/2004 | Pitroda et al. | |
| 6,715,679 B1 | 4/2004 | Infosino | |
| 6,722,570 B1 | 4/2004 | Eisele | |
| 6,755,341 B1 | 6/2004 | Wong et al. | |
| 6,764,005 B2 | 7/2004 | Cooper | |
| 6,769,618 B1 | 8/2004 | Finkelstein | |
| 6,805,288 B2 | 10/2004 | Routhenstein et al. | |
| 6,811,082 B2 | 11/2004 | Wong | |
| 6,813,354 B1 | 11/2004 | Jakobsson et al. | |
| 6,817,532 B2 | 11/2004 | Finkelstein | |
| 6,873,974 B1 | 3/2005 | Schutzer | |
| 6,902,116 B2 | 6/2005 | Finkelstein | |
| 6,970,070 B2 | 11/2005 | Juels et al. | |
| 6,980,969 B1 | 12/2005 | Tuchler et al. | |
| 6,985,583 B1 | 1/2006 | Brainard et al. | |
| 6,991,155 B2 | 1/2006 | Burchette, Jr. | |
| 7,013,030 B2 | 3/2006 | Wong et al. | |
| 7,030,860 B1 * | 4/2006 | Hsu .................... G06F 3/044 178/18.06 |
| 7,035,443 B2 | 4/2006 | Wong | |
| 7,039,221 B1 | 5/2006 | Tumey et al. | |
| 7,039,223 B2 | 5/2006 | Wong | |
| 7,044,394 B2 | 5/2006 | Brown | |
| 7,051,929 B2 | 5/2006 | Li | |
| 7,083,094 B2 | 8/2006 | Cooper | |
| 7,097,108 B2 | 8/2006 | Zellner et al. | |
| 7,100,049 B2 | 8/2006 | Gasparini et al. | |
| 7,100,821 B2 | 9/2006 | Rasti | |
| 7,111,172 B1 | 9/2006 | Duane et al. | |
| 7,114,652 B2 | 10/2006 | Moullette et al. | |
| 7,136,514 B1 | 11/2006 | Wong | |
| 7,140,550 B2 | 11/2006 | Ramachandran | |
| 7,163,153 B2 | 1/2007 | Blossom | |

(56) References Cited

U.S. PATENT DOCUMENTS

| | | |
|---|---|---|
| 7,195,154 B2 | 3/2007 | Routhenstein |
| 7,197,639 B1 | 3/2007 | Juels et al. |
| 7,219,368 B2 | 5/2007 | Juels et al. |
| 7,225,537 B2 | 6/2007 | Reed |
| 7,225,994 B2 | 6/2007 | Finkelstein |
| 7,246,752 B2 | 7/2007 | Brown |
| 7,298,243 B2 | 11/2007 | Juels et al. |
| 7,334,732 B2 | 2/2008 | Cooper |
| 7,337,326 B2 | 2/2008 | Palmer et al. |
| 7,346,775 B2 | 3/2008 | Gasparini et al. |
| 7,347,382 B2 | 3/2008 | Ferber et al. |
| 7,356,696 B1 | 4/2008 | Jakobsson et al. |
| 7,357,319 B1 | 4/2008 | Lin et al. |
| 7,359,507 B2 | 4/2008 | Kaliski |
| 7,360,688 B1 | 4/2008 | Harris |
| 7,363,494 B2 | 4/2008 | Brainard et al. |
| 7,364,092 B2 * | 4/2008 | Narendra et al. ............ 235/494 |
| 7,380,710 B2 | 6/2008 | Brown |
| 7,398,253 B1 | 7/2008 | Pinnell |
| 7,404,087 B2 | 7/2008 | Teunen |
| 7,424,570 B2 | 9/2008 | D'Albore et al. |
| 7,427,033 B1 | 9/2008 | Roskind |
| 7,454,349 B2 | 11/2008 | Teunen et al. |
| 7,461,250 B1 | 12/2008 | Duane et al. |
| 7,461,399 B2 | 12/2008 | Juels et al. |
| 7,472,093 B2 | 12/2008 | Juels |
| 7,472,829 B2 | 1/2009 | Brown |
| 7,494,055 B2 | 2/2009 | Fernandes et al. |
| 7,502,467 B2 | 3/2009 | Brainard et al. |
| 7,502,933 B2 | 3/2009 | Jakobsson et al. |
| 7,503,485 B1 | 3/2009 | Routhenstein |
| 7,516,492 B1 | 4/2009 | Nisbet et al. |
| 7,523,301 B2 | 4/2009 | Nisbet et al. |
| 7,530,495 B2 | 5/2009 | Cooper |
| 7,532,104 B2 | 5/2009 | Juels |
| 7,543,739 B2 | 6/2009 | Brown et al. |
| 7,559,464 B2 | 7/2009 | Routhenstein |
| 7,562,221 B2 | 7/2009 | Nystrom et al. |
| 7,562,222 B2 | 7/2009 | Gasparini et al. |
| 7,580,898 B2 | 8/2009 | Brown et al. |
| 7,584,153 B2 | 9/2009 | Brown et al. |
| 7,591,416 B2 | 9/2009 | Blossom |
| 7,591,426 B2 | 9/2009 | Osterweil et al. |
| 7,591,427 B2 | 9/2009 | Osterweil |
| 7,602,904 B2 | 10/2009 | Juels et al. |
| 7,621,458 B2 | 11/2009 | Zellner et al. |
| 7,631,804 B2 | 12/2009 | Brown |
| 7,639,537 B2 | 12/2009 | Sepe et al. |
| 7,641,124 B2 | 1/2010 | Brown et al. |
| 7,660,902 B2 | 2/2010 | Graham et al. |
| 7,690,580 B2 | 4/2010 | Shoemaker |
| 7,793,851 B2 | 9/2010 | Mullen |
| 7,828,207 B2 | 11/2010 | Cooper |
| 7,828,220 B2 | 11/2010 | Mullen |
| 7,931,195 B2 | 4/2011 | Mullen |
| 7,954,705 B2 | 6/2011 | Mullen |
| 7,954,708 B2 | 6/2011 | Blossom |
| 8,226,001 B1 | 7/2012 | Foo et al. |
| 8,302,872 B2 | 11/2012 | Mullen |
| 8,376,239 B1 | 2/2013 | Humphrey |
| 8,678,276 B2 | 3/2014 | Poidomani et al. |
| 2001/0034702 A1 | 10/2001 | Mockett et al. |
| 2001/0047335 A1 | 11/2001 | Arndt et al. |
| 2002/0032657 A1 | 3/2002 | Singh |
| 2002/0043566 A1 * | 4/2002 | Goodman et al. ............ 235/492 |
| 2002/0059114 A1 | 5/2002 | Cockrill et al. |
| 2002/0071385 A1 | 6/2002 | Ebara |
| 2002/0082989 A1 | 6/2002 | Fife et al. |
| 2002/0096570 A1 | 7/2002 | Wong et al. |
| 2002/0120583 A1 | 8/2002 | Keresman, III et al. |
| 2002/0153424 A1 | 10/2002 | Li |
| 2003/0034388 A1 | 2/2003 | Routhenstein et al. |
| 2003/0052168 A1 | 3/2003 | Wong |
| 2003/0057278 A1 | 3/2003 | Wong |
| 2003/0116635 A1 | 6/2003 | Taban |
| 2003/0152253 A1 | 8/2003 | Wong |
| 2003/0163287 A1 | 8/2003 | Vock et al. |
| 2003/0169039 A1 | 9/2003 | Kang et al. |
| 2003/0173409 A1 | 9/2003 | Vogt et al. |
| 2003/0178495 A1 | 9/2003 | Jones et al. |
| 2003/0179909 A1 | 9/2003 | Wong et al. |
| 2003/0179910 A1 | 9/2003 | Wong |
| 2003/0205624 A1 | 11/2003 | Huang et al. |
| 2003/0209608 A1 | 11/2003 | Blossom |
| 2003/0218066 A1 | 11/2003 | Fernandes et al. |
| 2003/0226899 A1 | 12/2003 | Finkelstein |
| 2004/0011877 A1 | 1/2004 | Reppermund |
| 2004/0026495 A1 | 2/2004 | Finkelstein |
| 2004/0035942 A1 | 2/2004 | Silverman |
| 2004/0133787 A1 | 7/2004 | Doughty |
| 2004/0145858 A1 | 7/2004 | Sakurada |
| 2004/0159700 A1 | 8/2004 | Khan et al. |
| 2004/0162732 A1 | 8/2004 | Rahim et al. |
| 2004/0172535 A1 | 9/2004 | Jakobsson |
| 2004/0177045 A1 | 9/2004 | Brown |
| 2004/0251303 A1 | 12/2004 | Cooper |
| 2005/0001711 A1 | 1/2005 | Doughty et al. |
| 2005/0043997 A1 | 2/2005 | Sohata et al. |
| 2005/0080747 A1 | 4/2005 | Anderson et al. |
| 2005/0086160 A1 | 4/2005 | Wong et al. |
| 2005/0086177 A1 | 4/2005 | Anderson et al. |
| 2005/0092830 A1 | 5/2005 | Blossom |
| 2005/0116026 A1 | 6/2005 | Burger et al. |
| 2005/0119940 A1 | 6/2005 | Concilio et al. |
| 2005/0133590 A1 | 6/2005 | Rettenmyer et al. |
| 2005/0139685 A1 | 6/2005 | Kozlay |
| 2005/0154643 A1 | 7/2005 | Doan et al. |
| 2005/0168345 A1 * | 8/2005 | Swafford et al. .......... 340/686.1 |
| 2005/0194452 A1 | 9/2005 | Nordentoft et al. |
| 2005/0211785 A1 | 9/2005 | Ferber et al. |
| 2005/0219728 A1 | 10/2005 | Durbin et al. |
| 2005/0228959 A1 | 10/2005 | D'Albore et al. |
| 2005/0247787 A1 | 11/2005 | von Mueller et al. |
| 2005/0274803 A1 | 12/2005 | Lee |
| 2006/0000900 A1 | 1/2006 | Fernandes et al. |
| 2006/0037073 A1 | 2/2006 | Juels et al. |
| 2006/0041759 A1 | 2/2006 | Kaliski et al. |
| 2006/0085328 A1 | 4/2006 | Cohen et al. |
| 2006/0091223 A1 | 5/2006 | Zellner |
| 2006/0124756 A1 | 6/2006 | Brown |
| 2006/0131393 A1 | 6/2006 | Cok et al. |
| 2006/0161435 A1 | 7/2006 | Atef et al. |
| 2006/0161789 A1 | 7/2006 | Doughty et al. |
| 2006/0163353 A1 | 7/2006 | Moulette et al. |
| 2006/0174104 A1 | 8/2006 | Crichton et al. |
| 2006/0186209 A1 | 8/2006 | Narendra et al. |
| 2006/0196931 A1 | 9/2006 | Holtmanns et al. |
| 2006/0249574 A1 | 11/2006 | Brown et al. |
| 2006/0256961 A1 | 11/2006 | Brainard et al. |
| 2006/0283958 A1 | 12/2006 | Osterweil |
| 2007/0023532 A1 | 2/2007 | Narendra et al. |
| 2007/0034700 A1 | 2/2007 | Poidomani et al. |
| 2007/0063025 A1 | 3/2007 | Blossom |
| 2007/0114274 A1 | 5/2007 | Gibbs et al. |
| 2007/0124321 A1 | 5/2007 | Szydlo |
| 2007/0131759 A1 | 6/2007 | Cox et al. |
| 2007/0136211 A1 | 6/2007 | Brown et al. |
| 2007/0152070 A1 | 7/2007 | D'Albore |
| 2007/0152072 A1 | 7/2007 | Frallicciardi et al. |
| 2007/0153487 A1 | 7/2007 | Frallicciardi et al. |
| 2007/0164101 A1 | 7/2007 | Meyerhofer |
| 2007/0174614 A1 | 7/2007 | Duane et al. |
| 2007/0192249 A1 | 8/2007 | Biffle et al. |
| 2007/0241183 A1 | 10/2007 | Brown et al. |
| 2007/0241201 A1 | 10/2007 | Brown et al. |
| 2007/0256123 A1 | 11/2007 | Duane et al. |
| 2007/0291753 A1 | 12/2007 | Romano |
| 2008/0005510 A1 | 1/2008 | Sepe et al. |
| 2008/0008315 A1 | 1/2008 | Fontana et al. |
| 2008/0008322 A1 | 1/2008 | Fontana et al. |
| 2008/0010675 A1 | 1/2008 | Massascusa et al. |
| 2008/0016351 A1 | 1/2008 | Fontana et al. |
| 2008/0019507 A1 | 1/2008 | Fontana et al. |
| 2008/0028447 A1 | 1/2008 | O'Malley et al. |

(56) References Cited

U.S. PATENT DOCUMENTS

| | | |
|---|---|---|
| 2008/0035738 A1 | 2/2008 | Mullen |
| 2008/0040271 A1 | 2/2008 | Hammad et al. |
| 2008/0040276 A1 | 2/2008 | Hammad et al. |
| 2008/0058016 A1 | 3/2008 | Di Maggio et al. |
| 2008/0059379 A1 | 3/2008 | Ramaci et al. |
| 2008/0065555 A1 | 3/2008 | Mullen |
| 2008/0093467 A1 | 4/2008 | Narendra et al. |
| 2008/0096326 A1 | 4/2008 | Reed |
| 2008/0116285 A1 | 5/2008 | Shoemaker |
| 2008/0121726 A1 | 5/2008 | Brady et al. |
| 2008/0126398 A1 | 5/2008 | Cimino |
| 2008/0128515 A1 | 6/2008 | Di Iorio |
| 2008/0148394 A1 | 6/2008 | Poidomani et al. |
| 2008/0150123 A1 | 6/2008 | Li et al. |
| 2008/0201264 A1 | 8/2008 | Brown et al. |
| 2008/0209550 A1 | 8/2008 | Di Iorio |
| 2008/0223937 A1 | 9/2008 | Preta et al. |
| 2008/0288699 A1 | 11/2008 | Chichierchia |
| 2008/0290166 A1 | 11/2008 | von Mueller |
| 2008/0294930 A1 | 11/2008 | Varone et al. |
| 2008/0302869 A1 | 12/2008 | Mullen |
| 2008/0302876 A1 | 12/2008 | Mullen |
| 2008/0302877 A1 | 12/2008 | Musella et al. |
| 2008/0314976 A1 | 12/2008 | Capurso et al. |
| 2009/0006262 A1 | 1/2009 | Brown et al. |
| 2009/0013122 A1 | 1/2009 | Sepe et al. |
| 2009/0036147 A1 | 2/2009 | Romano |
| 2009/0046522 A1 | 2/2009 | Sepe et al. |
| 2009/0048971 A1 | 2/2009 | Hathaway et al. |
| 2009/0055893 A1 | 2/2009 | Manessis et al. |
| 2009/0108064 A1 | 4/2009 | Fernandes et al. |
| 2009/0145964 A1 | 6/2009 | Blythe |
| 2009/0150295 A1 | 6/2009 | Hatch et al. |
| 2009/0152365 A1 | 6/2009 | Li et al. |
| 2009/0153297 A1 | 6/2009 | Gardner |
| 2009/0159696 A1 | 6/2009 | Mullen |
| 2009/0159702 A1 | 6/2009 | Mullen |
| 2009/0159709 A1 | 6/2009 | Mullen |
| 2009/0164380 A1 | 6/2009 | Brown |
| 2009/0173785 A1 | 7/2009 | Cooper |
| 2009/0200367 A1 | 8/2009 | Arnouse |
| 2009/0242648 A1 | 10/2009 | Di Sirio et al. |
| 2009/0244858 A1 | 10/2009 | Di Sirio et al. |
| 2009/0253460 A1 | 10/2009 | Varone et al. |
| 2009/0255996 A1 | 10/2009 | Brown et al. |
| 2009/0290704 A1 | 11/2009 | Cimino |
| 2009/0303885 A1 | 12/2009 | Longo |
| 2009/0308921 A1 | 12/2009 | Mullen |
| 2010/0270373 A1 | 10/2010 | Poidomani et al. |
| 2011/0062239 A1 | 3/2011 | Lau et al. |
| 2011/0272471 A1 | 11/2011 | Mullen |
| 2011/0272472 A1 | 11/2011 | Mullen |
| 2011/0272478 A1 | 11/2011 | Mullen |
| 2011/0276424 A1 | 11/2011 | Mullen |
| 2011/0276425 A1 | 11/2011 | Mullen |
| 2012/0187199 A1 | 7/2012 | Poidomani et al. |
| 2012/0205450 A1 | 8/2012 | Poidomani et al. |
| 2012/0280033 A1 | 11/2012 | Mitchell et al. |
| 2012/0280782 A1 | 11/2012 | Ross et al. |
| 2013/0320080 A1 | 12/2013 | Olson et al. |
| 2013/0335542 A1 | 12/2013 | Li |

FOREIGN PATENT DOCUMENTS

| | | |
|---|---|---|
| JP | 05210770 A | 8/1993 |
| WO | WO9852735 | 11/1998 |
| WO | WO0247019 | 6/2002 |
| WO | WO2006066322 | 6/2006 |
| WO | WO2006080929 | 8/2006 |
| WO | WO2006105092 | 10/2006 |
| WO | WO2006116772 | 11/2006 |
| WO | WO2007141779 | 12/2007 |
| WO | PCT/US11/25047 | 2/2011 |

OTHER PUBLICATIONS

U.S. Appl. No. 60/675,388, Poidomani et al.
The Bank Credit Card Business. Second Edition, American Bankers Association, Washington, D.C., 1996.
A Day in the Life of a Flux Reversal. http://www.phrack.org/issues.html?issue=37&id=6#article. As viewed on Apr. 12, 2010.
Dynamic Virtual Credit Card Numbers. http://homes.cerias.purdue.edu/~jtli/paper/fc07.pdf. As viewed on Apr. 12, 2010.
USPTO, International Search Report, Apr. 28, 2009.
English translation of JP 05210770 A.
EPO, Extended European Search Report, Jan. 26, 2012.
AU, Patent Examination Report No. 1, Oct. 11, 2012.
EPO, Article 94(3) Communication, Feb. 5, 2013.
EPO, Rule 115(1) Summons to Oral Proceedings, Sep. 18, 2013.
Magnetic Stripe Card. http://en.wikipedia.org/w/index.php?title=Magnetic_stripe_card&oldid= 174608901. Dated Nov. 29, 2007. See EPO, Article 94(3) Communication, Feb. 5, 2013.

* cited by examiner

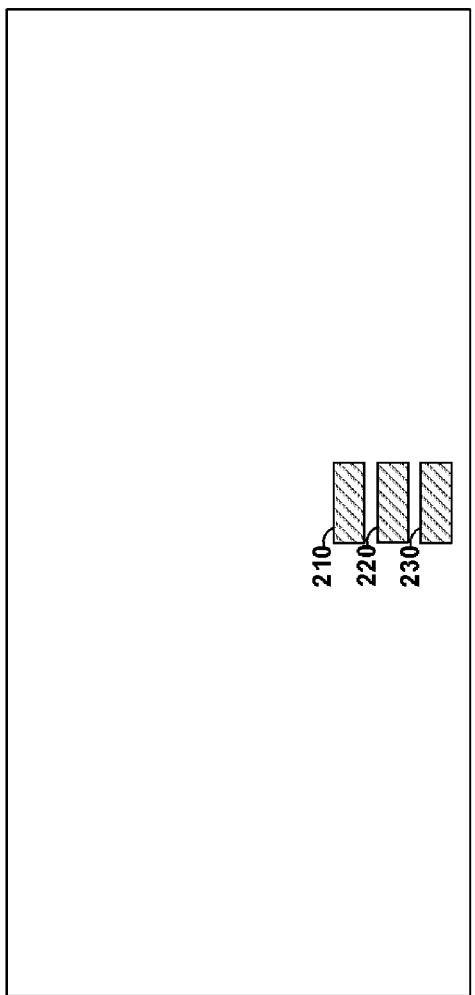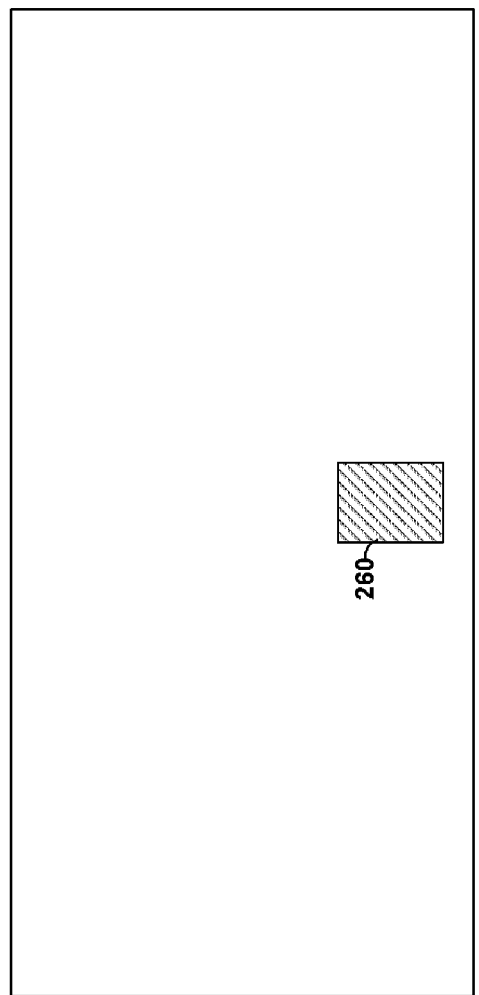

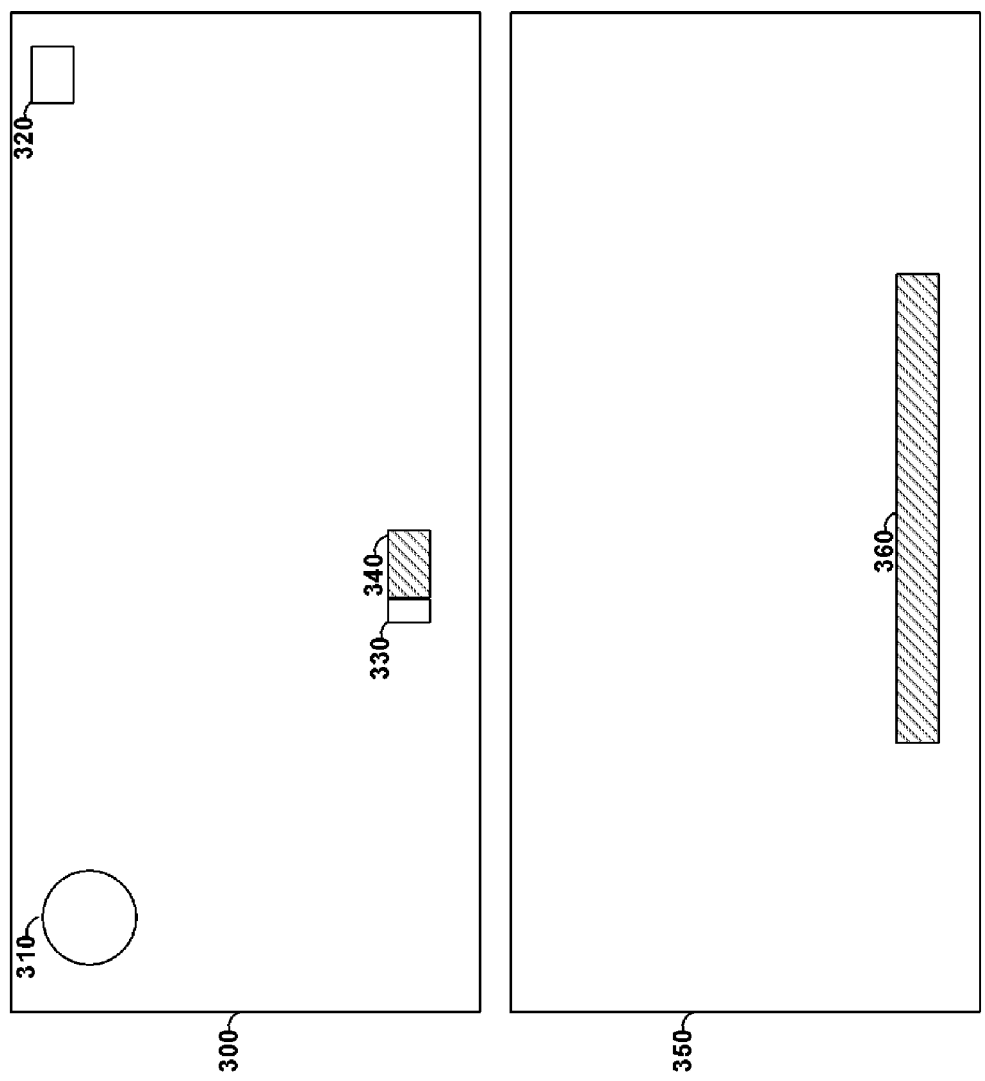

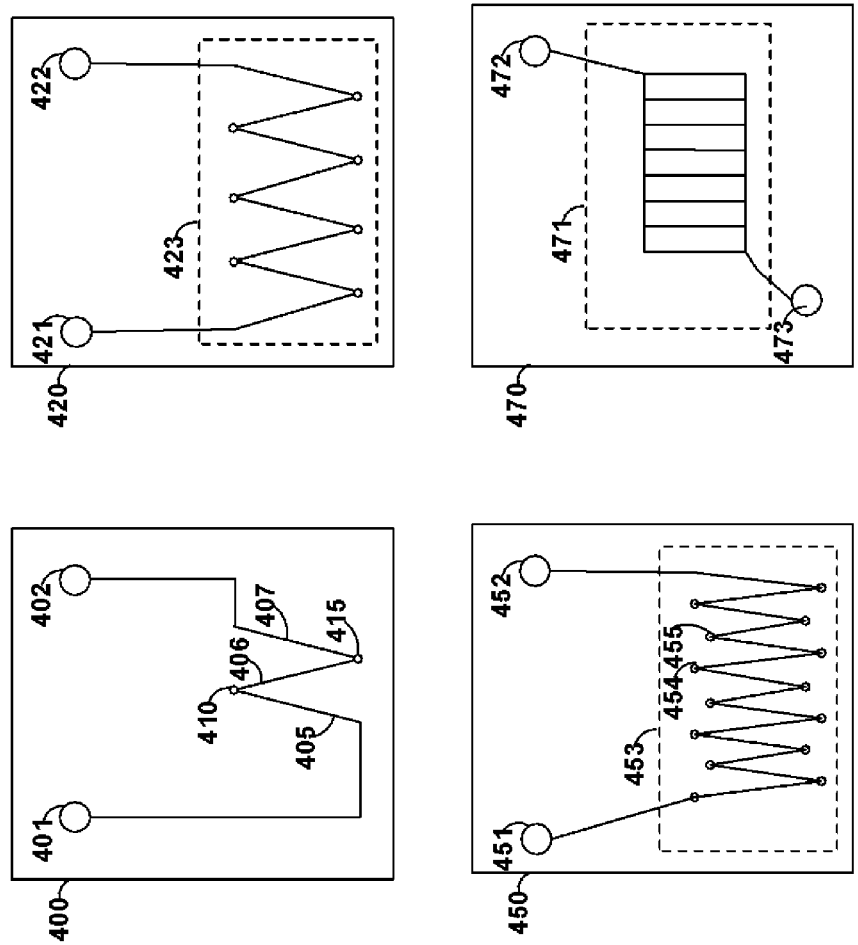

CARDS WITH SERIAL MAGNETIC EMULATORS

CROSS-REFERENCE TO RELATED APPLICATIONS

This application is a continuation of U.S. patent application Ser. No. 12/339,042, filed on Dec. 19, 2008, which claims the benefit of U.S. Provisional Patent Application No. 61/016,491 filed on Dec. 24, 2007, 61/026,846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008, 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to cards such as payment cards.

SUMMARY OF THE INVENTION

A card, or other device, is provided with a magnetic emulator operable to communicate with a magnetic stripe reader. The emulator may be operable to communicate a block of information serially such that a reader may sense the emulator and the information may be transmitted through the emulator serially. Accordingly, the emulator may comprise of, for example, a single wire or coil and may transmit bits one-by-one at high frequencies such that all information in a block is transmitted to a magnetic stripe reader while the read head of the reader is in the proximity of the single wire or coil. An emulator may also be provided in a parallel configuration such that multiple bits of data are emulated at the same time. For example, a parallel emulator may include 3000 regions to emulate 3000 bits simultaneously while a serial emulator may include a single region to communicate the 3000 bits in rapid succession.

A card, or other device, having a magnetic emulator may take the form of, for example, a credit card, debit card, security card, and/or any other type of card. Accordingly, the dynamic information may be a dynamic credit card number, a dynamic debit card number, a dynamic security number, or any other type of dynamic number. A display may be provided to display the data, or a portion of the data, communicated through an emulator or additional data. For example, a one type of security code may be displayed on a display and another type of security code may be communicated through a magnetic emulator.

A payment card, such as a credit card, may be provided that includes a display. All, or a portion of, a payment card number (e.g., a credit card) may, for example, be changed periodically and displayed on the display. Similarly, this changed information may be emulated via a parallel or serial emulator. A magnetic encoder may also be utilized to erase and write information to a magnetic medium.

A parallel or serial emulator may be located next to one or more magnetic stripe segments (e.g., sandwiched between two magnetic stripe segments). A magnetic stripe may be utilized to transmit static information such that power is conserved. For example, if the beginning bits of a data block must take a particular form (e.g., start bits followed by user identification information) then this information may be embodied as a magnetic stripe. A serial or parallel emulator may then be provided to communicate the remaining information of the block (e.g., dynamic credit card number).

Numerous types of structures may be utilized to determine when a read head of a magnetic stripe reader is reading, or is about to read, a magnetic stripe or a dynamic magnetic communications device (e.g., a magnetic emulator or encoder). Such structures may be utilized to turn a magnetic emulator, such as a serial magnetic emulator, ON. By only turning an emulator ON when the emulator is in the proximity of a magnetic stripe reader, power may be conserved. For example, a button may be provided on a card, or other device, such that a user may provide manual input to instruct the card, or other device, to turn an emulator ON. Alternatively, for example, one or more sensors may be provided to determine the presence of a read-head of a magnetic stripe reader. For example, a hall-effect sensor may be provided to detect a magnetic field's interaction with a read-head, a circuit may be provided to detect the presence of a conductive material, and/or a circuit may be provided to detect the capacitance of a particular material. Alternatively still, for example, the swiping motion of a card may be detected via one or more inertial sensors such as accelerometers and/or gyroscopes. Upon the initiation of turning an emulator ON, the emulator may be driven through a routine (e.g., repeatedly emulating the same block of information serially for a period of time or for a number of data transmissions). A card, or other device, may include, for example, a magnetic stripe section, followed by a read head detector, followed by a serial or parallel encoder. A second magnetic stripe section may follow the serial or parallel encoder (e.g., and another read head detector may precede the encoder to determine when the read head is not reading the encoder).

An emulator may be fabricated using a PCB printing technique. Such a technique may provide the emulator on, for example, a PCB board (e.g. FR4 board). Any additional components may be fabricated on the flexible PCB board. For example, a processor, display, and emulator may be fabricated on the same flexible PCB board. Such a flexible PCB board may be coupled to a flexible battery and hot-film laminated or cold laminated (e.g., injection molding) to form a card. The flexible PCB board and flexible battery may be placed into any housing of any device.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which:

FIG. 2 is an illustration of cards constructed in accordance with the principles of the present invention;

FIG. 3 is an illustration of cards constructed in accordance with the principles of the present invention;

FIG. 4 is an illustration of emulators constructed in accordance with the principles of the present invention;

DETAILED DESCRIPTION OF THE INVENTION

Figure 1:
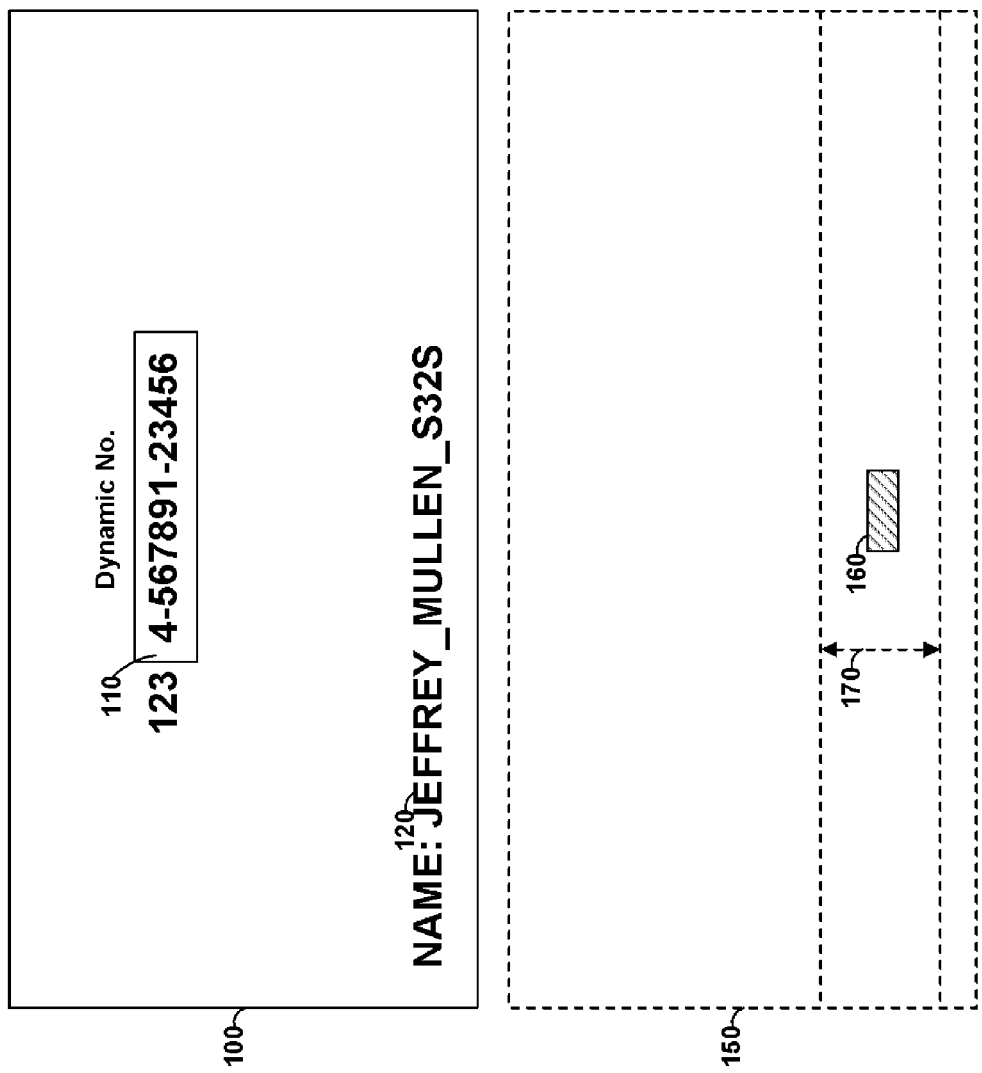
FIG. 1 is an illustration of cards constructed in accordance with the principles of the present invention.

FIG. 1 shows card 100 that may include a display that displays dynamic number 110, which may be utilized, for example, as part of a credit card number (e.g., with a static portion of a credit card number that proceeds dynamic number 110). Persons skilled in the art will appreciate that a dynamic number may take any forms such as, for example, a dynamic credit card number, a dynamic verification code number, and/or a dynamic security code number. For example, card 100 may include a dynamic credit card number and a dynamic verification code (e.g., a 15 digit credit card number and a 4 digit verification code).

Identification information 120 may be provided on card 100. Accordingly, for example, a dynamic number may be provided for a particular period of time according to a coding scheme for that particular period of time. Thus, the identification information, time, and dynamic information may be transmitted via manual entry (e.g., through an online store) or via a magnetic emulator (e.g., through a magnetic stripe reader). A remote server may receive such information and verify whether the dynamic information is correct for particular identification information and a particular period of time.

Card 150 is provided and may include magnetic emulator 160 instead of magnetic stripe 170. Persons skilled in the art will appreciate that magnetic emulator 160 may be embedded behind a magnetic stripe or may be located next to a magnetic stripe. Magnetic emulator 160 may take many forms. For example, magnetic emulator 160 may include any number of emulation segments (e.g., one or more wires or coils) to emulate a particular bit or number of bits of information.

Emulator 160 may include a single emulation segment and may communicate a block of information serially by communicating bits at a high data transmission rate. Accordingly, a serial emulator may be provided.

Emulator 160 may include multiple emulation segments— each of which may, for example, simultaneously emulate a different bit of information. Accordingly, a parallel emulator may be provided.

Emulator 160 may include multiple emulation segments— each of which may, for example, emulate the same bit of information. Accordingly, a serial emulator may be provided. Such a serial emulator may, for example, allow for a larger area to be read by a reader. In doing so, for example, a read head may be located over emulator 160 for a longer period of time such that more information may be read by a read-head for a particular period of time.

FIG. 2 shows card 200, which may include any number of emulators. For example, card 200 may include emulator 210, 220, and 230. Each of emulators 210, 220, and 230 may, for example, be a serial emulator. Such emulators may be vertically aligned or vertically staggered. Persons skilled in the art will appreciate that by providing multiple emulators, multiple tracks of a magnetic stripe may be simultaneously emulated.

A magnetic stripe reader may, for example, determine information on a magnetic stripe by detecting the frequency of changes in magnetic fields (e.g., flux transversals). A particular frequency of flux transversals may correlate to, for example, a particular information state (e.g., a logic "1" or a logic "0"). Accordingly, for example, a magnetic emulator may change the direction of an electromagnetic field at particular frequencies in order to communicate a different state of information (e.g., a logic "1" or a logic "0").

Persons skilled in the art will appreciate that a magnetic emulator may electromagnetically communicate information serially by changing the magnitude of an electromagnetic field with respect to time. As such, for example, a current in a single direction may be provided through a magnetic emulator in order for that magnetic emulator to generate an electromagnetic field of a single direction and a particular magnitude. The current may then be removed from the magnetic emulator such that, for example, the electromagnetic field is removed. The creation of a presence of an electromagnetic field, and the removal of that electromagnetic field, may be utilized to communicate information to, for example, a magnetic stripe reader. A magnetic stripe reader may be configured to read, for example, the change in flux versus time and may associate an increase in an electromagnetic field (e.g., creation of a field) as one flux transversal and a decrease (e.g., removal of a field) as another transversal. In doing so, for example, driving circuitry (not shown) may be provided which, in turn, controls when current is provided to a magnetic emulator. The timing of magnetic flux transversals, as determined by a magnetic stripe reader, may be utilized by that reader to determine whether a logic one ("1") or logic zero ("0") was communicated. Accordingly, a driving circuit may change the frequency of when current is supplied and removed from a magnetic emulator in order to communicate a logic one ("1") or a logic zero ("0").

A driving circuit may, for example, change the direction of current supplied to a magnetic emulator to increase the amount of change in an electromagnetic field magnitude for a period of time. In doing so, for example, a magnetic stripe reader may more easily be able to discern overall changes in an electromagnetic field and, as such, may more easily be able to discern information. As such, for example, a driving circuit may increase the magnitude of an electromagnetic field by providing negative current, decrease the amount of negative current until no current is provided and provide an increasing positive current in order to provide a large swing in the magnitude of an electromagnetic field. Similarly, a driving circuit may switch from providing one amount of negative current (or positive current) to one amount of positive current (or negative current).

Persons skilled in the art will appreciate that a string of a particular bit of data (e.g., a string of logic zeros "0s") may be communicated before as well as after information is communicated through a magnetic emulator. A magnetic stripe reader may utilize such data, for example, to determine base timing information such that the magnetic stripe reader has a timing reference that the reader can utilize to assist in determining timing changes of perceived flux transversals. Accordingly, for example, a magnetic emulator may send data at different overall frequencies and a magnetic stripe reader may be able to reconfigure itself to receive data at such overall frequencies. Information may be encoded using, for example, Frequency/Double Frequency (F2F) encoding such that magnetic stripe readers may perform F2F decoding.

A processor may control one or more emulators by, for example, controlling the direction of the current supplied through one or more segments of an emulator. By changing the direction of current through a region, for example, the direction of an electromagnetic field may be changed. Similarly, a processor may control one or more emulators by, for example, controlling the change in magnitude of current supplied through one or more segments of an emulator. As such, for example, a processor may increase the magnitude of current as well as decrease the magnitude of current supplied through an emulator. A processor may control the timing of such increases and decreases in current such that a magnetic emulator may, for example, communicate F2F encoded information.

Card 250 may be provided and may include emulator 260. Emulator 260 may be configured so that it can be read by more than one read heads. For example, emulator 260 may be configured so that it can be read by three read heads. Accordingly, one region may be utilized to communicate the same information across all three read heads simultaneously. Emulator 260 may, for example, cycle through transmitting information from each track such that all tracks are communicated serially. Such tracks may be communicated with bits identifying each track such that processing connected to each read-head can determine the information desired to be communicated to each particular read-head. As such, a magnetic stripe reader may be configured to receive the multiple tracks (e.g., tracks 1 and 2) through each read-head such that the magnetic stripe reader receives four tracks of data. The magnetic stripe reader may then, for example, utilize identification bits (e.g., start sentinels) in each track to identify the received track. Similarly, for example, the magnetic stripe reader may be configured to recognize that multiple instances of the same track were received and only forward a single instance of each received track to a processor. Persons skilled in the art will appreciate that different tracks may be communicated with the same identification bits. Accordingly, for example, a magnetic stripe reader may be configured to determine the identity of tracks by performing additional computations. For example, the magnetic stripe reader may be configured to check all of the information sent in those tracks and, if the information is the same, a single instance may be provided to subsequent processing. Additionally, for example, the magnetic stripe reader may be configured to determine the length of tracks with the same identification bits (e.g., start sentinels) to determine whether different tracks were communicated. Similarly, a single emulator that sequentially communicates multiple different tracks of information to a single read-head may, for example, change the timing of each communicated track such that processing coupled to the single read-head discerns just the single track that the read-head expected to receive.

Persons skilled in the art will appreciate that a magnetic stripe on a card may be of a particular density having a fixed amount of bits. A serial emulator, for example, may communicate more than this fixed amount of bits by, for example, increasing the rate at which bits are serially communicated. A serial emulator may, for example, communicate a format code that a reader may utilize to discern the length of the communicated information. For example, a serial emulator may communicate a track of information that is greater than, approximately, 750 bits in length, 1,000 bits in length, or 2,000 bits in length. Any number of bits may define, for example, a character (e.g., 4-bit characters, 5-bit characters, 6-bit characters, 7-bit characters, or 8-bit characters).

FIG. 3 shows card 300 that may include structures to determine when card 300 is being read by a magnetic stripe reader. Card 300 may include magnetic emulator 340. For example, card 300 may include button 310 that may be pressed in order to initiate an emulator such as emulator 340. Emulator 340 may be configured to turn ON while button 310 is pressed. Alternatively, for example, emulator 340 may be configured to turn ON when button 310 is pressed for a particular period of time, to transmit a particular sequence of data (e.g., information including a number that changes with every button press), and/or a particular number of repetitions of a sequence of the same data. Persons skilled in the art will appreciate that if a button press of button 310 is associated with turning emulator 340 ON for a particular period (e.g., more than 1 second but less than 5 seconds) of time then, for example, emulator 340 may only turn ON for a relatively short period of time (or not at all) when button 310 is accidently pressed down for a relatively long period of time. Inertial movement sensor 320 may be included to detect a swipe in order to initiate one or more emulators. Inertial movement sensor 320 may include, for example, any number of accelerometers and/or gyroscopes. Read-head sensor 330 may be included to detect when a read head of a magnetic stripe reader is about to pass over, or is passing over, emulator 340. Persons skilled in the art will appreciate that multiple read head sensors 330 may be located (e.g., aligned vertically) adjacent to emulator 340 as different sensors may detect different types of readers. Additionally, for example, one or more sensors may be placed on the other side of emulator 340 such that emulator 340 is sandwiched between sensors. In this manner, for example, emulator 340 may be triggered regardless of the direction that card 300 is swiped. Sensors may include, for example, hall-effect sensors, capacitive sensors, and/or conductive material sensors. Conductive material sensors may detect conductive material by closing an electrical loop that uses the conductive material to close the electrical loop.

Card 350 may include emulator 360. Emulator 360 may extend, for example, along the majority of the length of card 350 (or approximately all of card 350). Emulator 360 may be a parallel emulator or, for example, may be a serial emulator. For example, emulator 360 may be a coil such that a single bit is emulated by emulator 360 at a time. Such an emulator 380 may, for example, switch bits being emulated at a high rate so that a read-head of a magnetic stripe reader can receive a large amount of information while the read-head of the magnetic stripe reader is located over emulator 360.

FIG. 4 shows emulators 400, 420, 450, and 470. Emulator 400 may include, for example, contacts 401 and 402 that may provide a current through conductive segments 405, 406, and 407 in a particular direction. Particularly, for example, a voltage may be applied across contacts of a particular polarity to provide a current in a particular direction (given the particular resistance of the emulator). Driving circuitry may be coupled to one or more contacts for providing a particular current (e.g., of a particular direction and/or particular magnitude). Information may be communicated by, for example, supplying current to and emulator, and removing the current supply from the emulator, in a fashion that results in communicating information to a magnetic stripe reader through electromagnetic fields provided by the emulator. Additional circuitry may be provided to control different attributes of an electrical signal provided to conductive segments 405, 406, and 407. For example, a transistor may be provided to assist with controlling the magnitude of a current that reaches conductive segments 405, 406, and 407.

Emulator 400 may be fabricated, for example, using any fabrication technique such as a printed circuit board fabrication technique (e.g., utilizing FR4). Via 410 and via 415 may be included to electrically couple conductive segments 405 and 407 to conductive segment 406. Accordingly, for example, conductive segment 406 may be provided at a different height then conductive segment 405 and conductive segment 407 (e.g., with respect to a base). For example, conductive segments 405 and 407 may be provided one surface of a material while conductive segment 406 is provided on another surface of a material. Segment 405 and 407 may be located closer to the reverse side of a card while segment 406 may be located closer to the obverse side of a card (or vise versa). Accordingly, for example, wire segments 405, 406, and 407 may take on a three-dimensional shape and particular segments (e.g., wire segment 406) may be closer to a particular surface than other segments. Persons skilled in the art will appreciate that segment 406 may be angled (e.g., with respect to a top or bottom edge of a card) or may be in parallel (with respect to a top or bottom edge of a card). An emulator may include multiple instances of emulator 400 coupled in, for example, a series configuration. Conductive segments on the same surface of a material may be, for example, spaced uniformly on that surface. Accordingly, for example, a coil may be provided as an emulator with numerous turns and a current may be provided through that emulator such that an electromagnetic field is generated that is operable to be sensed by a magnetic stripe reader.

Persons skilled in the art will appreciate that numerous vias and line segments may be provided such that conductive segments are provided at several heights. Thus, for example, a coil may be fabricated on a multiple layer board. Emulator 400 may be utilized, for example, to transmit information serially. For example, the direction of the electromagnetic field created by line segments 405, 406, and 407 may be changed. Control circuitry may, in turn, change the direction of the electromagnetic field (e.g., by changing the direction of the current) at different frequencies such that a reader configured to detect the frequency of field reversals (e.g., using F2F decoding) can receive information. As such, emulator 400 may communicate multiple bits of data serially by utilizing line segments 405, 406, and 407. Any number of line segments may be added. Additionally, for example, only a single conductive segment may be provided. Furthermore, multiple instances of emulator 400 may be placed next to each other and may be separately controlled. In doing so, for example, multiple, independent electromagnetic fields may be controlled such that different information may be emulated simultaneously (e.g., in parallel).

Conductive segments may, for example, be printed on a board (e.g., a flexible PCB board) in a conductive material (e.g., a metal). Similarly, vias may be provided and filled to provide conductive interconnects. Multiple layers may be printed to provide a three-dimensional PCB. Persons skilled in the art will appreciate, however, that an emulator may be provided on a single layer with any number of conductive segments (e.g., one or more than one).

Emulator 420 may be provided and may include conductive segment array 423. Person skilled in the art will appreciate that conductive segment array 423 may be fabricated in multiple layers to form a coil. Accordingly, the coil may be provided with a current of a particular direction and may generate an associated electromagnetic field across the coil. Additionally, for example, current may be provided and removed from emulator 420 to communicate information. In extending the length of an array (e.g., adding more segments or increasing the space of segments), the amount of time a read head is operable to read information from an array may be increased.

Emulator 450 may be provided and may include contacts 451 and 452 to provide a current (e.g., a current of a particular direction) to conductive segment array 453. Persons skilled in the art will appreciate that conductive segments in array 453 may be coupled to vias that are not horizontally aligned with one another. Accordingly, the vias may be staggered. In doing so, for example, the conductive segments may be spaced closer together as vias may be spaced closer together. For example, by staggering the lengths of line segments, vias 454 and 455 may be able to be provided at larger densities. In turn, a coil may be provided with an increased number of turns.

Emulator 470 may be provided and may include array 471 controlled by contacts 472 and 473. Vertical conductive segments may, for example, be controlled together or may be controlled independently (e.g., by having a separate pair of contacts for each vertical conductive segment). Components may be provided on each segment in order to, for example, provide current through each segment. For example, resistors may be added to each segment. The resistors of each segment may be different. For example, the resistance of each segment may be configured to be substantially equal. Multiple emulators may be utilized on a structure (e.g., a card or other device) to communicate to, for example, communicate to different read heads or the same read head.

Figure 5:
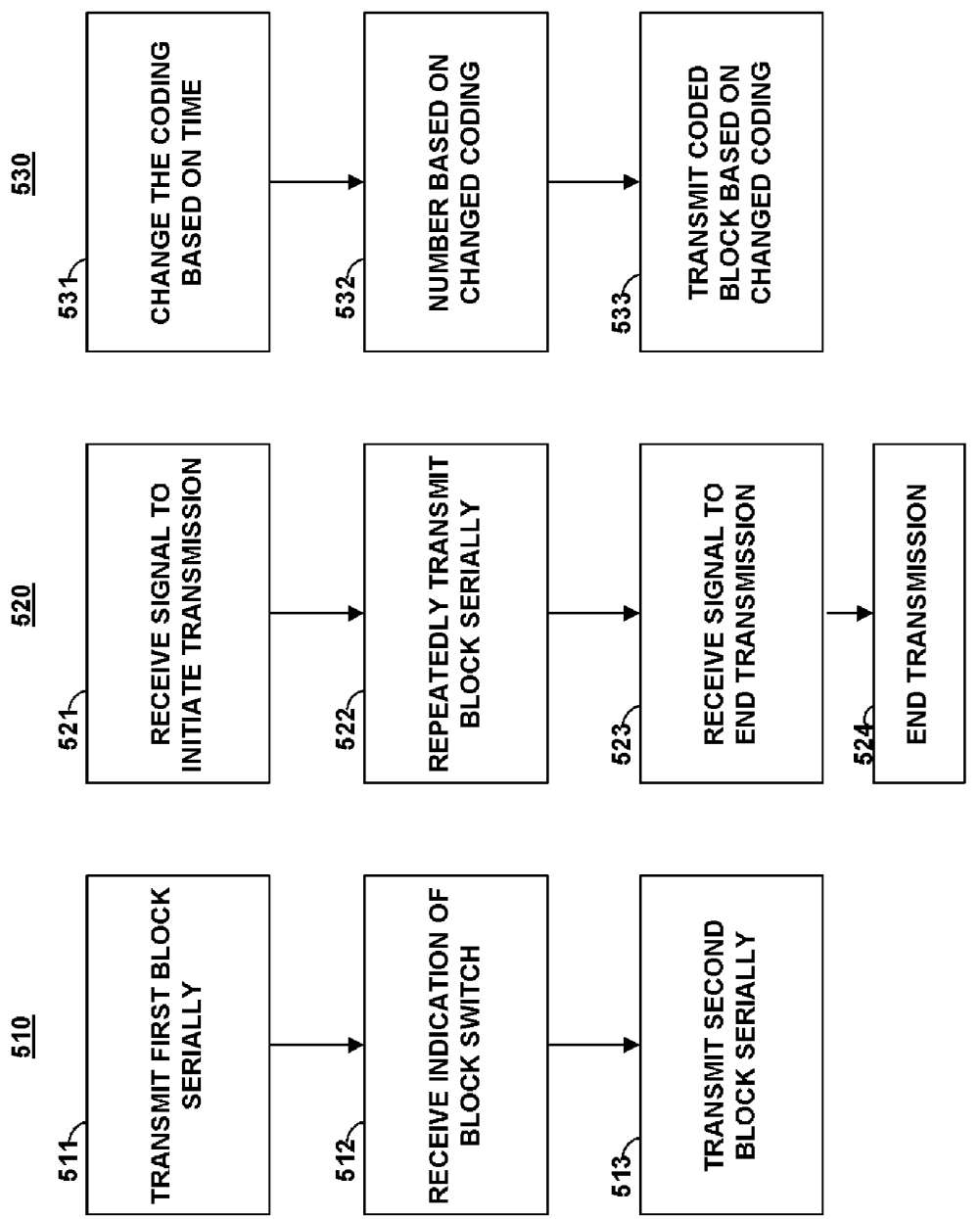
FIG. 5 is an illustration of process topologies constructed in accordance with the principles of the present invention.

FIG. 5 shows flow charts 510, 520, and 530. Flow chart 510 may be utilized in a card or any other device (e.g., a token or personal electronic device). Step 510 may be utilized to transmit a first block of data (e.g., track 1 credit card information). Step 512 may then receive an indication to switch the data block that is being communicated. Such a switch may be done autonomously through processing logic or manually through a manual interface such as a button. Step 513 may provide a second block of data (e.g., track 2 credit card information). In this manner, for example, an emulator may provide different types of data in different types of formats and at different data block lengths.

Flow chart 520 may be provided and may include step 521, in which a signal is received to initiate a transmission. Such a transmission may take the form of an emulation and may be triggered autonomously through software (e.g., the detection of a read head) or manually through a manual interface (e.g., one or more buttons). Step 522 may initiate and repeatedly send a block of data serially. Step 523 may initiate and a signal may be received to end a transmission. Such a signal may be provided, for example, autonomously through software (e.g., the detection of a read-head by a second detector circuit after an emulator) or manually through a manual interface (e.g., on or more buttons. Transmission may be ended in step 524.

Persons skilled in the art will appreciate that a read-head detector may be utilized to cause a magnetic emulator to, for example, transmit a block of information serially (e.g., payment information) once each time the read-head detector senses a read-head. Alternatively, for example, a read-head detector may be utilized to cause a magnetic emulator to, serially transmit the same block of information repeatedly a particular number of times or for a particular period of time. Pauses may be introduced between transmissions of the block of information (e.g., payment information). Any dynamic magnetic communications device (e.g., one or more emulators and/or encoders) may be utilized based on the readings of one or more read-head detectors.

Flow chart 530 may be provided. Step 531 may, for example, change the coding of a number based on time (e.g., may code a credit card number differently with respect to time). Accordingly, a number may be changed based on the changed coding in step 532. The coded block may be transmitted in step 533. Persons skilled in the art will appreciate that a number (e.g., a dynamic number) may be provided visual via a display as well as magnetically via an emulator. Such a visual and emulation display may occur simultaneously. A different manual interface may be utilized (e.g., a different button) to turn a display ON or to turn an emulator ON.

Persons skilled in the art will appreciate that a particular magnetic stripe track (e.g., track 2 of a payment card such as a credit card) may have a particular amount of information at a particular density and in a particular format. For example, an emulator may transmit 40 characters, where each character is represented by 5 bits, by transmitting 200 bits. A magnetic stripe may include a track with, for example, 400 magnetic regions that may represent a maximum of approximately 400 flux reversals. Persons skilled in the art will appreciate that, furthering this example, with serial transmission, all 400 flux reversals (or more) may be transmitted by a single region. If start bits are utilized in a data block, then, for example, the data block may be repeatedly sent and resent and be properly utilized by a reader. For example, if a reader picks up a serial transmission in the middle of a transmission, the reader may not recognize the start bits and may wait until a start bits are received. Thus, an emulator may be driven such that it can, for example, send a data block approximately at least twice (e.g., approximately 800 associated flux reversals if a block is associated with 400 flux reversals) while a read-head of a magnetic stripe reader is operable to communicate with an emulator (e.g., the read-head is located over the emulator). In doing so, for example, an emulator may be able to transmit a block regardless of when a read head starts reading a block.

A magnetic stripe reader may, for example, be configured such that it is able to sense approximately at least 30,000 flux changes per second. Accordingly, an emulator region may transmit, for example, two blocks of information (e.g., of 400 transversals) to such a reader in approximately 0.0266 seconds. If, for example, the region is approximately 1 mm wide, the user may be operable to swipe at approximately 0.037 meters/second (approximately 1.5 inches/second) and the information may be communicated to a reader. If, for example, the region is approximately 5 mm wide, the user may swipe at approximately 7.5 inches/second and the information may be communicated to a reader. Persons skilled in the art will appreciate that larger currents may be utilized to drive larger regions. Persons skilled in the art will appreciate that users may be able to swipe at a variety of speeds, and may change the speed of the swipe while a card is being read by a reader, and an emulator may still properly transmit information via emulation. An emulator may be provided, for example, such that a user may swipe at speeds up to at least approximately 0.5, 1, 5, 10 feet/second for a particular reader (e.g., a reader operable of reader 30,000 flux changes a second).

Persons skilled in the art will appreciate that a number of manufacturing techniques may be utilized. An emulator may provide a uniform field for a particular distance about the surface of a card, but may be able to rapidly change the direction of the field. A coil may be provided using a two-layer or several-layer PCB techniques. Persons skilled in the art will appreciate that the width of a conductive segment (e.g., a wire trace) may be approximately 0.003 inches (or larger) and the diameter of vias connecting layers may be approximately 0.008 inches (or larger). Additionally, for example, a pattern of concentric rectangles may be utilized to produce a desired field in serial (or in parallel, for example, if multiple are utilized) transmission scheme. A single trace may also be split into multiple parallel traces that collective generate a desired field pattern.

Figure 6:
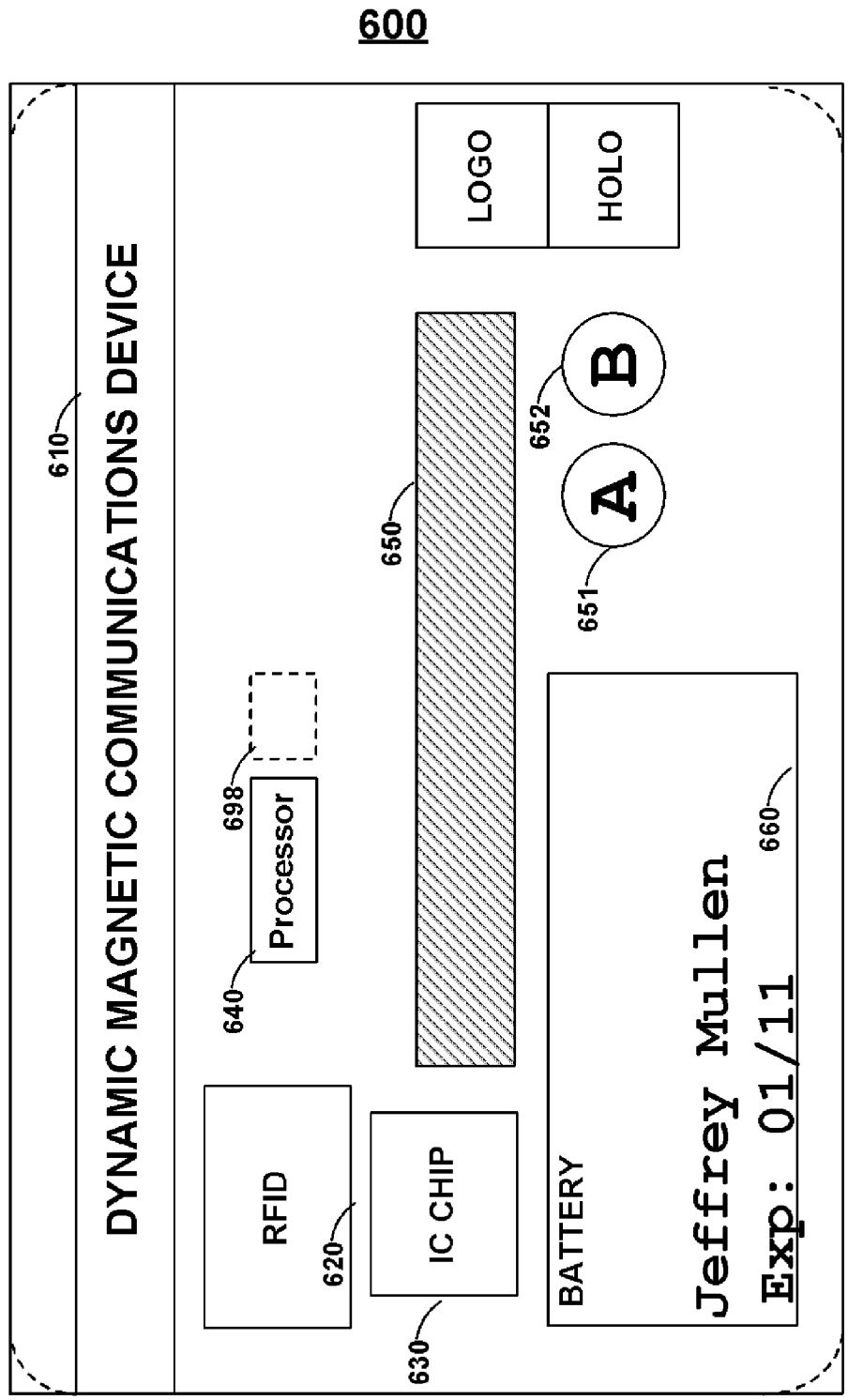
FIG. 6 is an illustration of a card constructed in accordance with the principles of the present invention.

FIG. 6 shows card 600 that may include, for example, one or more IC chips 630 (e.g., EMV chips), RFID antennas 620, processors 640, displays 650, dynamic magnetic communications devices 610 (e.g., magnetic encoders and/or magnetic emulators), batteries 660, and buttons 651 and 652. Additional circuitry 698 may be provided which may be, for example, one or more oscillators or emulator driving circuits. Persons skilled in the art will appreciate that button 651 may, for example, be utilized by a user to select one encryption algorithm for a number displayed on display 650 while button 652 may be utilized by a user to select a different encryption algorithm. Persons skilled in the art will appreciate that the components of card 600 may be provided on either surface of a card (e.g., a front or rear surface of the card) or inside of a card. A logo (e.g., of a card issuer) and logo may be provided on either surface of a card.

A button, such as button 651, may be utilized, for example, to display a number. Such a number may be, for example, encrypted from a secure number based on time or use. For example, one-time use numbers (e.g., a payment number or code) may be retrieved from a list of numbers on memory each time button 651 is pressed and displayed on display 650. A processor may only go through each number once on a list. A registration process may be provided in which a user may be requested to enter in a sequence of numbers such that a remote server may validate the card and learn where in a sequence of a list a card currently resides. Numbers may be repeated on a list or may only occur once on a list. All of the numbers available by the length of the number may be utilized by the list or only a portion of the numbers available by the length of the number may be provided by the list. A secret number may be encrypted on a card and a verification server may also have knowledge of this secret number. Accordingly, the remote server may perform the same encryption function as the card on the secret number and verify that the resultant encrypted number is the same as the resultant encrypted number on a card. Alternatively, for example, the remote server may decrypt the received encrypted number to determine the authenticity of the encrypted number and validate an activity (e.g., validate a security access request or a purchase transaction).

Figure 7:
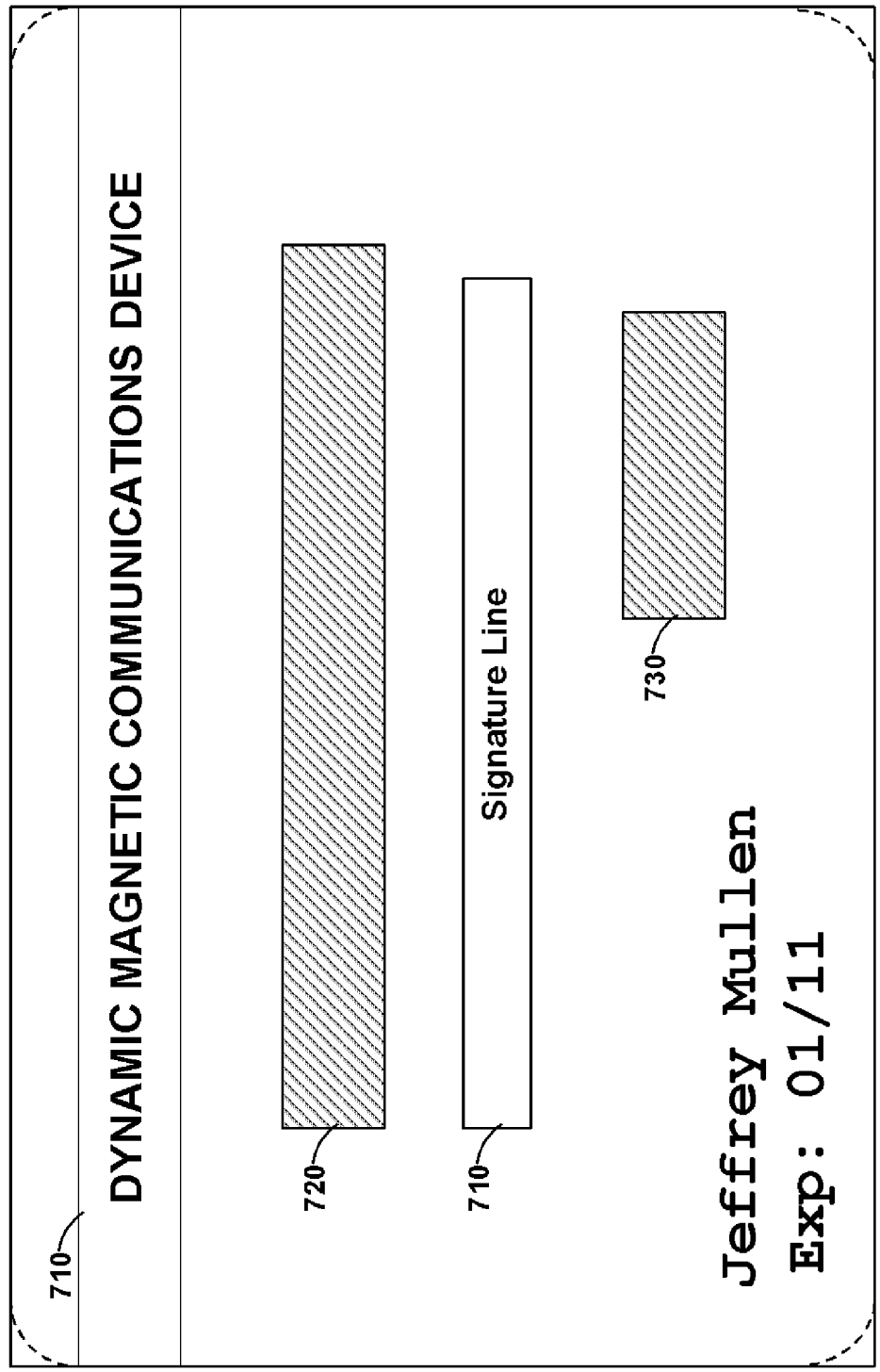
FIG. 7 is an illustration of a card constructed in accordance with the principles of the present invention.

FIG. 7 shows card 700 that may include, for example, signature area 710 that may include a material operable to receive marks from a pen (e.g., a signature). Card 700 may also include, for example, displays 720 and 730. Display 720 may, for example, display a payment number while display 730 displays a security code (e.g., for online purchase authentication). Display 720 as well as display 730 may be utilized on the same side as, for example, dynamic magnetic communications device 710.

Figure 8:
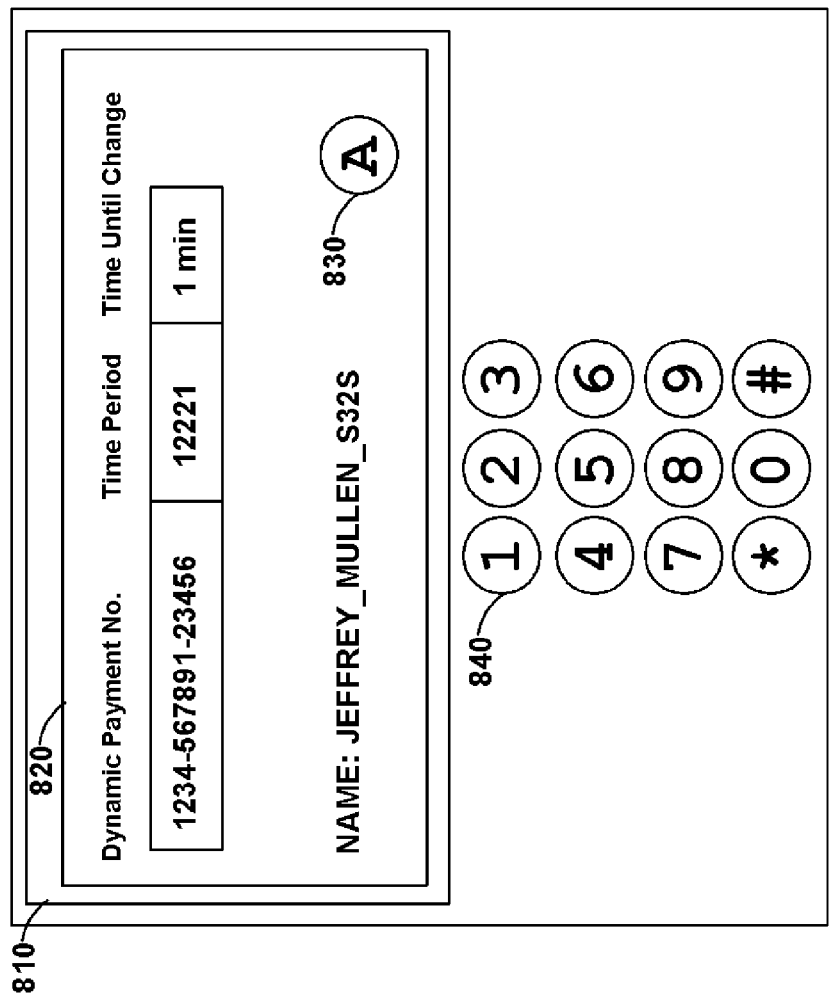
FIG. 8 is an illustration of a personal electronic device constructed in accordance with the principles of the present invention.

FIG. 8 shows personal electronic device 800 which may be, for example, a portable telephonic device, portable media player, or any type of electronic device. Persons skilled in the art will appreciate that the functionality of a card may be provided on a personal device and displayed through a graphical user interface. Personal electronic device 800 may include, for example, user inputs 840 and display 810. Virtual card 820 may be displayed on display 820. Display 820 may be a touch-sensitive display such that, for example, virtual button 830 may be provided on virtual card 820. Persons skilled in the art will appreciate that cards may be provided as virtual cards and a user may interact with such virtual cards in order to provide a variety of functions. Personal electronic device 800 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:

1. A card comprising:
   an electronic device operable to communicate first information to a read-head of a magnetic stripe reader;
   a first capacitive sensor;
   a second capacitive sensor;
   a third capacitive sensor; and
   a fourth capacitive sensor, wherein said first, second, third, and fourth capacitive sensors are utilized to detect said read-head.

2. The card of claim 1, further comprising a battery.

3. The card of claim 1, further comprising a processor.

4. The card of claim 1, further comprising a second electronic device operable to communicate second information.

5. The card of claim 1, wherein said electronic device is fabricated on a several layer flexible printed circuit board.

6. The card of claim 1, wherein said electronic device is fabricated on a flexible printed circuit board.

7. The card of claim 1, further comprising a battery and a processor.

8. The card of claim 1, further comprising an RFID.

9. The card of claim 1, further comprising a processor and an integrated circuit chip.

10. The card of claim 1, further comprising a second electronic device and a third electronic device.

11. The card of claim 1, further comprising a display.

12. The card of claim 1, wherein said electronic device includes a coil that is fabricated on a two-layer flexible printed circuit board.

13. The card of claim 1, further comprising a second electronic device fabricated on a several layer flexible printed circuit board and a third electronic device fabricated on said several layer flexible printed circuit board.

14. The card of claim 1, further comprising a second electronic device fabricated on a flexible printed circuit board and a third electronic device fabricated on said flexible printed circuit board.

15. The card of claim 1, wherein said first, second, third, and fourth capacitive sensors are aligned in proximity to said electronic device.

16. The card of claim 1, wherein said first and second capacitive sensors are aligned in proximity to a first end of said electronic device and said third and fourth capacitive sensors are aligned in proximity to a second end of said electronic device.

17. The card of claim 1, further comprising a button.

18. The card of claim 1, wherein said first, second, third, and fourth capacitive sensors are aligned adjacent to said electronic device to detect when said read head is about to pass over said electronic device.

19. The card of claim 1, wherein said first, second, third, and fourth capacitive sensors are aligned adjacent to said electronic device to detect when said read head is passing over said electronic device.

20. The card of claim 1, further comprising a plurality of buttons.

* * * * *